US00PP26250P2

(12) United States Plant Patent
Wells

(10) Patent No.: US PP26,250 P2
(45) Date of Patent: Dec. 22, 2015

(54) ***LITHODORA* PLANT NAMED 'MONRIK'**

(50) Latin Name: *Lithodora diffusa*
Varietal Denomination: MonRik

(71) Applicant: Rick Wells, McMinnville, OR (US)

(72) Inventor: Rick Wells, McMinnville, OR (US)

(73) Assignee: MONROVIA NURSERY COMPANY, Azusa, CA (US)

( * ) Notice: Subject to any disclaimer, the term of this patent is extended or adjusted under 35 U.S.C. 154(b) by 134 days.

(21) Appl. No.: 13/987,984

(22) Filed: Sep. 20, 2013

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — C. A. Whealy

(57) ABSTRACT

A new and distinct cultivar of *Lithodora* plant named 'MonRik', characterized by its compact, upright to somewhat outwardly spreading and uniformly mounded plant habit; freely branching habit; green and creamy white-colored variegated leaves; bright blue-colored flowers; and good garden performance.

1 Drawing Sheet

Botanical designation: *Lithodora diffusa.*
Cultivar denomination: 'MONRIK'.

BACKGROUND OF THE INVENTION

The present invention relates to a new and distinct cultivar of *Lithodora*, botanically known as *Lithodora diffusa* and hereinafter referred to by the name 'MonRik'.

The new *Lithodora* plant is a naturally-occurring branch mutation of *Lithodora diffusa* 'Grace Ward', not patented. The new *Lithodora* plant was discovered and selected by the Inventor on a single plant of 'Grace Ward' within a population of plants of 'Grace Ward' in a controlled greenhouse environment in Dayton, Oreg. on Mar. 1, 2011.

Asexual reproduction of the new *Lithodora* plant by vegetative cuttings in a controlled greenhouse environment in Dayton, Oreg. since May 1, 2011 has shown that the unique features of this new *Lithodora* plant are stable and reproduced true to type in successive generations.

SUMMARY OF THE INVENTION

The new *Lithodora* plant has not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'MonRik'. These characteristics in combination distinguish 'MonRik' as a new and distinct *Lithodora* plant:

1. Compact, upright to somewhat outwardly spreading and uniformly mounded plant habit.
2. Freely branching habit.
3. Green and creamy white-colored variegated leaves.
4. Bright blue-colored flowers.
5. Good garden performance.

Plants of the new *Lithodora* differ from plants of the parent, 'Grace Ward', primarily in leaf color as plants of 'Grace Ward' have solid green-colored leaves.

Plants of the new *Lithodora* can be compared to plants of the *Lithodora diffusa* 'White Star', disclosed in U.S. Plant Pat. No. 20,078. In side-by-side comparisons conducted in Dayton, Oreg., plants of the new *Lithodora* differed from plants of 'White Star' in the following characteristics:

1. Plants of the new *Lithodora* and 'White Star' differed in leaf color as plants of 'White Star' had solid green-colored leaves.
2. Plants of the new *Lithodora* and 'White Star' differed in flower color as plants of 'White Star' had blue and white bi-colored flowers.

BRIEF DESCRIPTION OF THE PHOTOGRAPHS

The accompanying colored photographs illustrate the overall appearance of the new *Lithodora* showing the colors as true as it is reasonably possible to obtain in colored reproductions of this type. Colors in the photographs may differ slightly from the color values cited in the detailed botanical description which accurately describe the colors of the new *Lithodora.*

The photograph at the bottom of the sheet comprises a side perspective view of a typical flowering plant of 'MonRik' grown in a container.

The photograph at the top of the sheet is a close-up view of a typical flowering plant of 'MonRik'.

DETAILED BOTANICAL DESCRIPTION

The aforementioned photographs and following observations, measurements and values describe plants grown during the summer in one-gallon containers in a shadehouse in Dayton, Oreg. and under cultural practices typical of commercial *Lithodora* production. During the production of the plants, day temperatures averaged 28° C. and night temperatures averaged 11° C. Plants were one year old when the photographs and the description were taken. In the description, color references are made to The Royal Horticultural Society Colour Chart, 2007 Edition, except where general terms of ordinary dictionary significance are used.

Botanical classification: *Lithodora diffusa* 'MonRik'.

Parentage: Naturally-occurring branch mutation of *Lithodora diffusa* 'Grace Ward', not patented.

Propagation:

*Type*.—By vegetative cuttings.

*Time to initiate roots, summer*.—About three weeks at 24° C.

*Time to initiate roots, winter*.—About five weeks at 16° C.

*Time to produce a rooted young plant, summer*.—About three months at 24° C.

*Time to produce a rooted young plant, winter*.—About six months at 16° C.

*Root description*.—Fine, fibrous; light brown to white in color.

*Rooting habit*.—Freely branching; dense.

Plant description:

*Plant form and growth habit*.—Herbaceous perennial; compact, upright to somewhat outwardly spreading and uniformly mounded plant habit; freely branching habit, about five primary lateral branches develop, each with multiple secondary and tertiary branches; moderately vigorous growth habit.

*Plant height*.—About 12.5 cm.

*Plant width* (*spread*).—About 27 cm.

*Lateral branches*.—Length: About 15 cm. Diameter: About 2.5 mm. Internode length: About 7 mm. Strength: Strong. Texture: Pubescent; becoming woody with development. Color, young stems: Close to 195A. Color, woody stems: Close to N200A.

Leaf description:

*Arrangement*.—Alternate, simple; sessile.

*Length*.—About 1.5 cm to 1.8 cm.

*Width*.—About 4 mm.

*Shape*.—Oblong to slightly lanceolate.

*Apex*.—Broadly acute to rounded.

*Base*.—Clasping.

*Margin*.—Entire.

*Texture, upper and lower surfaces*.—Pubescent, hirsute.

*Venation pattern*.—Single midvein.

*Color*.—Developing leaves, upper surface: Centers, close to 138A to 138B; towards the margins, close to 150D. Developing leaves, lower surface: Centers, close to 147C to 147D; towards the margins, close to 150D. Fully expanded leaves, upper surface: Centers, close to 137B; towards the margins, close to 158C; venation, close to 147B. Fully expanded leaves, lower surface: Centers, close to 147B; towards the margins, close to 158C; venation, close to 137B.

Flower description:

*Flower type and flowering habit*.—Terminal and axillary single tubular flowers; usually about eight flowers developing per lateral branch; flowers face upright and outwardly; flowers sessile.

*Fragrance*.—None detected.

*Natural flowering season*.—Plants flower continuously from late April to late July in Oregon.

*Postproduction longevity*.—Flowers last about five days on the plant; flowers not persistent.

*Flower buds*.—Height: About 1 cm. Diameter: About 3 mm. Shape: Oblong to elongate. Color: Close to 96D.

*Flower diameter*.—About 1.2 cm.

*Flower length*.—About 1.4 cm.

*Flower throat diameter*.—About 2 mm.

*Flower tube length*.—About 1.2 cm.

*Flower tube diameter*.—About 2 mm.

Petals.—Quantity per flower: Typically five fused at the base in a narrow tube. Lobe length: About 6 mm. Lobe width: About 4 mm. Lobe shape: Roughly oblong. Lobe apex: Rounded. Margin: Entire. Texture, upper surface: Smooth, glabrous. Texture, lower surface: Scattered pubescence. Color: When opening, upper surface: Close to 99C. When opening, lower surface: Close to 98A. Fully opened, upper surface: Close to 100A; along midvein, close to 99C; color does not fade with development. Fully opened, lower surface: Close to 99D. Throat: Close to 93C to 93D. Tube: Close to 93A; at the base, close to 157B.

*Sepals*.—Quantity per flower: Typically five in a single whorl fused at the base. Length: About 8 mm. Width: About 1 mm. Shape: Lanceolate. Apex: Acute. Margin: Entire. Texture, upper and lower surfaces: Pubescent. Color, upper and lower surfaces: Close to 150D.

*Reproductive organs*.—Stamens: Quantity per flower: Typically five. Filament length: About 5 mm; adnate to throat. Filament color: Close to 84B. Anther shape: Oval. Anther length: About 1 mm. Anther color: Close to 161A. Pollen amount: Scarce. Pollen color: Close to 162D. Pistils: Quantity per flower: One. Pistil length: About 1.2 cm. Stigma shape: Bi-parted. Stigma color: Close to 157D. Style length: About 1 cm. Style color: Close to 157D. Ovary color: Close to 145D.

*Fruits and seeds*.—Fruit and seed development have not been observed on plants of the new *Lithodora*.

Disease & pest resistance: Plants of the new *Lithodora* have not been noted to be resistant to pathogens and pests common to *Lithodora*.

Garden performance: Plants of the new *Lithodora* have been observed to have good garden performance and tolerate rain, wind and temperatures ranging from about 3° C. to about 23° C. Plants of the new *Lithodora* are suitable for USDA Hardiness Zones 6 through 9.

It is claimed:

1. A new and distinct *Lithodora* plant named 'MonRik' as illustrated and described.

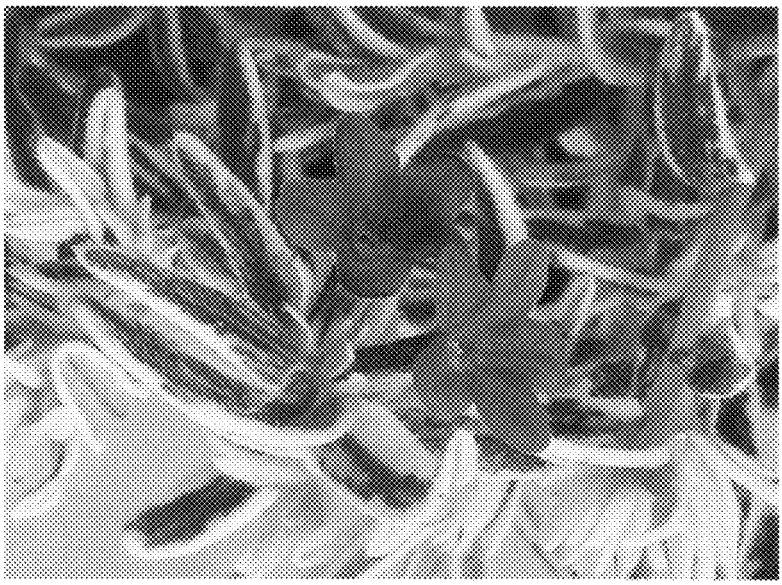
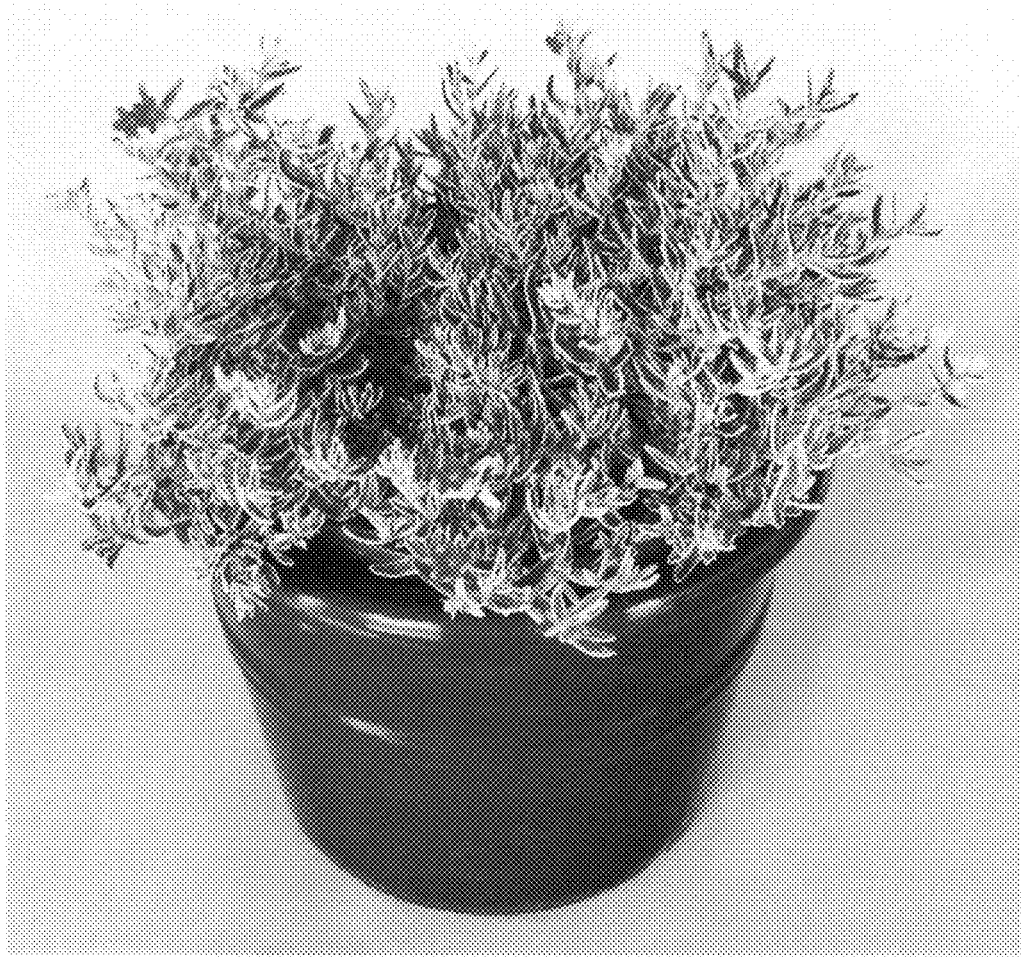

* * * * *